US005746945A

United States Patent [19]
Ryklin et al.

[11] Patent Number: 5,746,945
[45] Date of Patent: May 5, 1998

[54] WATER-IN-OIL EMULSIONS CONTAINING INCREASED AMOUNTS OF OIL AND METHODS FOR PREPARING SAME

[75] Inventors: Irma Ryklin, Buffalo Grove; Branko Sajic, Lincolnwood, both of Ill.

[73] Assignee: Stepan Company, Northfield, Ill.

[21] Appl. No.: 608,276

[22] Filed: Feb. 28, 1996

Related U.S. Application Data

[63] Continuation-in-part of Ser. No. 163,981, Dec. 6, 1993, abandoned.

[51] Int. Cl.$^6$ ............................................ B01J 13/00
[52] U.S. Cl. ................... 252/309; 106/2; 252/314; 424/70.12; 424/70.121; 508/208; 514/937
[58] Field of Search ........................ 252/309, 314; 514/937; 106/2; 424/70.12, 70.121; 508/208

[56] References Cited

U.S. PATENT DOCUMENTS

| | | | |
|---|---|---|---|
| 4,013,475 | 3/1977 | Liebowitz et al. | 106/10 |
| 4,152,416 | 5/1979 | Spitzer et al. | 424/46 |
| 4,532,132 | 7/1985 | Keil | 514/937 X |
| 4,675,422 | 6/1987 | Bernhardt et al. | 556/13 |
| 4,724,174 | 2/1988 | Bernhardt et al. | 427/376.6 |
| 4,784,844 | 11/1988 | Thimineur et al. | 514/937 X |
| 4,839,167 | 6/1989 | Yamamoto et al. | 424/70.12 |
| 4,990,377 | 2/1991 | Wilson | 106/2 X |
| 5,015,415 | 5/1991 | Goze et al. | 252/547 |
| 5,162,378 | 11/1992 | Guthauser | 252/309 X |
| 5,188,823 | 2/1993 | Shapiro et al. | 424/65 |
| 5,262,087 | 11/1993 | Tachibana et al. | 252/309 |
| 5,302,323 | 4/1994 | Hartung et al. | 424/70.12 X |

FOREIGN PATENT DOCUMENTS 2056859   6/1992   Canada .

*Primary Examiner*—Richard D. Lovering
*Attorney, Agent, or Firm*—McDonnell Boehnen Hulbert & Berghoff

[57] ABSTRACT

Water-in-oil emulsions are disclosed that comprise
(a) water;
(b) from about 10 to 65% by weight of an oil; and
(c) an emulsification system comprising a polysiloxane polyalkyl polyether copolymer and a phthalic anhydride derivative, substantially permanently maintaining the water and oil as an emulsion, the emulsification system and the emulsification system being substantially free from aluminum and zirconium salts, the emulsion being at a pH of from about 5 to 10.

14 Claims, No Drawings

WATER-IN-OIL EMULSIONS CONTAINING INCREASED AMOUNTS OF OIL AND METHODS FOR PREPARING SAME

BACKGROUND OF THE INVENTION

This application is a continuation-in-part of U.S. application Ser. No. 08/163,981, filed Dec. 6, 1993, which is incorporated herein by reference in its entirety.

1. Field of the Invention

The present invention relates to water-in-oil emulsions containing increased amounts of an oil phase. More specifically, the invention relates to water-in-oil emulsions comprising oil and water phases and an emulsifier comprising a phthalic anhydride derivative that are stable at critical pH values.

2. Description of the Related Art

Water-in-oil emulsions have been employed in a wide variety of applications. Among these are polishes and waxes for hard surfaces of, for example, automobiles, shoes, and furniture. Water-in-oil emulsions are also used as antiperspirants, sunscreens, skin creams and lotions, and hair treatment compositions such as hair conditioners.

Incorporation of increased amounts of oil, and especially silicone oil, leads to difficulty in preparing stable water-in-oil formulations. It is particularly difficult to formulate stable water-in-oil emulsions having in excess of 50% by weight silicone oil. Thus, formulations of water-in-oil systems with oils such as silicones requires the use of an emulsification system capable of providing the requisite emulsion stability.

U.S. Pat. No. 5,188,823 discloses water-in-oil antiperspirant formulations comprising silicone oils, copolyols, phthalamic acids and/or ammonium phthalamates, and aluminum and zirconium antiperspirant salts. Water-in-oil formulations containing at most about 33% cyclomethiones are disclosed having viscosities ranging from about 2,700 to 14,000 cps. The pH of these water-in-oil formulations is from about 3.5 to 4.5.

U.S. Pat. No. 5,015,415 teaches conditioning shampoos comprising phthalamic acids and/or ammonium phthalamates and silicone oils. Shampoo formulations are disclosed with no more than 0.50% silicone oil. These formulations are taught to be stable at pH values between 3 and 9.

Canadian Patent Application 2,056,859 discloses hair treatment compositions comprising a water-in-oil emulsion, wherein the water phase constitutes 40–95% by weight of the composition and the oil phase 5–60% by weight of the composition, wherein the oil phase comprises a silicone material having a viscosity of $10^4$ to $10^9$ mPas at 25° C.

SUMMARY OF THE INVENTION

It has been unexpectedly discovered that stable water-in-oil emulsions can be prepared to contain in excess of about 50% by weight oil when the emulsion is formulated with a specific emulsification system and the resulting emulsion is at a specific critical pH. The emulsions of the invention can be prepared to contain any amount of an oil up to about 65% by weight of the formulation.

The water-in-oil emulsions encompassed by the invention comprise:
(a) water;
(b) from about 10 to 65% by weight of an oil; and
(c) an emulsification system comprising a polysiloxane polyalkyl polyether copolymer and a phthalic anhydride derivative, the emulsification system substantially permanently maintaining the water and oil as an emulsion, and the emulsification system being substantially free from aluminum and zirconium salts, the emulsion being at a pH of from about 5–10.

The invention encompasses stable water-in-oil emulsions having viscosities in the range of from about at least 1000, and preferably from about 1500 to $10^6$ cps. The invention also encompasses such emulsions that are pastes, i.e., emulsions that are typically not a pourable liquid at ambient temperature.

DETAILED DESCRIPTION OF THE INVENTION

Water-in-oil emulsions, and in particular, water-in-oil emulsions containing silicone, are difficult to prepare without separation into oil and water phases when the amount of the oil approaches 50% by weight. The present invention provides novel water-in-oil emulsions that are stable when containing more than 50% by weight of an oil phase. These emulsions employ an emulsification system comprising a specific phthalic anhydride derivative and a silicone glycol surfactant. Further, the pH of the emulsion must be within the critical range to obtain the requisite stability.

The Oil Phase

Water-in-oil compositions of the invention comprise from 5–65% by weight, more preferably from 10–65% by weight, most preferably 20–60% by weight of an oil phase. The oil phase may comprise any oily material that is immisible with water. Suitable oily materials are those having viscosities from about 0.1 to 10,000,000 cps. In preferred embodiments of the invention, the oily material is a silicone oil material.

The silicone material for use in compositions of the invention can be any silicone material of the required viscosity. For example, polyalkyl siloxanes, polyalkylaryl siloxanes, aminofunctional silicones, polydiorganosiloxanes or mixtures thereof may be used.

Silicone gums i.e., non volatile silicones, may be used as the silicone materials. For the purpose of the present invention, the term silicone gum denotes polydiorganosiloxanes having a molecular weight of 200,000 to 2,000,000. Examples of suitable silicone gums are for example described in U.S. Pat. No. 4,152,416. Specific examples of suitable silicone gums are polydimethyl or polydiphenyl siloxane polymers.

Such silicone materials for use in the compositions of the invention have a viscosity of $10^4$ to $10^9$ mpa.s at 25° C., more preferably from $5 \times 10^4$ to $5 \times 10^8$, most preferably from $10^5$ to $5 \times 10^7$ mpa.s. A suitable method for measuring the viscosity is by means of a glass capillary viscometer (of Dow Corning CTM 0004), or by a Brookfields synchrolectric viscometer (of Dow Corning CTM 0050).

In certain embodiments of the invention, the oil phases of compositions also comprise a carrier or diluent material for the high viscosity, non-volatile silicone material. Often, high viscosity silicone materials are supplied as a dispersion in a carrier or diluent material, for example as a 5–25% by weight dispersion of the high viscosity silicone in cyclomethicone, linear dimethicone and/or isoparaffin. These dispersions may advantageously be used in the oil phase of the hair treatment products of the invention. Alternatively or additionally the oil phase may comprise further diluents such as for example low viscosity silicones (having a viscosity of say between 0.1 to 1,000 mpa.s, more preferably 0.5 to 500 mPa.s most preferably 0.65–100), liquid paraffins or methicones and other solvents such as $C_{10}$ to $C_{12}$ isoparaffins such as Isopar L (Esso), polyisobutene such as polysynlane (Nippon Oils and Fats), squalane such as Squalene (J. G. Marthens), branched chain hydrocarbons e.g., Permethyl 99A (Presperse), branched chain light paraffin oils such as Lytol (Witco) or WM1 (BP), mineral oil such as Marchol 82 (Esso) or Carnation Oil (Witco), long chain alkyl alkanoic esters such as decyl oleate (e.g., Cetiol Vex Henkel), isopropyl myristate (e.g., Estol 1514 ex Unichema) and glyceryl tri(2-ethyl hexanoate) e.g., Myritol CTEG ex Henkel).

In preferred embodiments, the silicone oil will comprise a cyclomethicone or dimethicone. Generally such silicones may be represented by the formula:

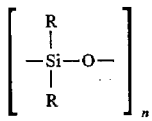

wherein R is a 1 to 3 carbon alkyl group, n is a number from 3 to 10, preferably from 3 to 7, and the unsatisfied valences on the oxygen and silicon atoms at the ends of the chain may be joined to one another to form a cyclic structure. Suitable volatile silicones are, for example, U.C.C. Y-7207, sold by Union Carbide Corporation in which each R is methyl and which typically comprises by weight 99.4% tetramer, 0.6% trimer and traces of the pentamer and hexamer; SWS-03314, sold by SWS Silicones, a Division of Stauffer Chemical Company, in which R is methyl and which is substantially all tetramner; and Dow Corning 344 fluid, sold by Dow Corning, Inc., in which R is methyl and which typically comprises by weight about 88% tetramer, about 11.8% pentamer and traces of trimer and hexamer.

In addition, other volatile silicones may also be utilized, alone or in combination with non-volatile silicones.

It is also possible to employ vegetable oils, animal oils, provided that branched-chain alkyl groups are present as well as various petroleum products and lubricants. Compositions may also be prepared to contain graphite lubricants, polybutene, polyethylene, linseed oil, and crude oil, as well as other oils and other solid or semi-solid materials.

The oils that may be used in the emulsions also include petroleum distillates, solvents and hydrocarbons such as, for example, mineral spirits, kerosene, terpenes, and glycol ethers.

The oils may also be materials suitable for personal care products, e.g., mineral oil, petrolatum, caprylic/capric triglyceride, isopropyl myristate, isopropyl palmitate, octyl palmitate, octyl isonononoate alkyl, esters of fatty acids having at least about 16 carbon atoms, lanolin, or alkyl esters of long chain fatty acids.

The oil phase normally is prepared to contain a phthalic anhydride derivative emulsifying agent. The phthalic anhydride derivative of the invention has the following formula:

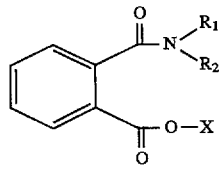

where X a cation is selected from the group consisting of hydrogen ion, $^+NH_2R_3R_4$ where $R_3$ and $R_4$ are the same or different and represent hydrogen or straight or branched chain alkyl groups having 8–40 carbon atoms, $[NH_3(R_5$ OH$)]^+$, $[NH_2(R_5OH)_2]^{++}$, $[NH(R_5OH)_3]^+$ where each $R_5$ is a straight or branched chain alkylene group having from 1–6 carbon atoms, $NH_4^+$, $R_7NH_3^+$, $(R_7)_2NH_2^+$, $(R_2)_3NH^+$ where each $R_7$ is straight or branched chain alkyl having from about 1 to 6 carbon atoms, $Na^+$, $K^+$, $Ba^{++}$, $Ca^{++}$, $Mg^{++}$, $Al^{2+}$, and $Zn^{2+}$, or $(R_7)_2NH_2^+$ represents a heterocyclic cation containing 4 or 5 carbon atoms that optionally contains an oxygen or an addditional nitrogen atom, $R_1$ and $R_2$ are the same or different and represent straight or branched chain alkyl groups having 1–40 carbon atoms, cycloalkyl groups having 3–18 carbon atoms, straight or branched chain alkenyl groups having 2–40 carbon atoms, alkylaryl groups where the alkyl portion is a straight or branched chain alkyl group having 1–6 carbon atoms and the aryl portion contains 5 to 10 carbon atoms, aryl alkyl where the alkyl portion is a straight or branched chain alkyl of 1–6 carbon atoms and the aryl portion contains 5 to 10 carbon atoms, or aryl groups having 5 to 10 carbon atoms, or $R_5$—O— $R_6$ where $R_5$ and $R_6$ are the same or different and represent straight or branched chain alkyl or alkenyl groups having 1–22 carbon atoms.

In a preferred emulsion of the invention, X is $^+NH_2R_3R_4$, and $R_1$, $R_2$, $R_3$, and $R_4$ are derived from hydrogenated tallow. Because tallow is a mixture of $C_{14}$ to $C_{18}$ fatty acids, and amines derived from tallow are hence a mixture of tallow amines, the phthalamic acids and/or the ammonium salts thereof used in the present invention may therefore have R groups that are the same or different.

In particularly preferred emulsions of the present invention, the formulations comprise N,N-di(hydrogenated) tallow phthalamic acid di(hydrogenated) tallow ammonium salt. In other particularly preferred embodiments, the formulations comprise a mixture of N,N-di(hydrogenated) tallow phthalamic acid and N,N-di(hydrogenated) tallow phthalamic acid di(hydrogenated) tallow ammonium salt. Other formulations comprise N,N-distearyl phthalamic acid and N,N-distearyl phthalamic acid N,N-distearyl ammonium salt where the stearyl groups are derived from a vegetable oil.

The effective concentration of these phthalamic acid ammonium salts and mixtures of the phthalamic acids and phthalamic acid ammonium salts in the emulsions of the present invention vary from about 1% to about 20% on an active basis. A presently preferred use concentration appears to be between about 1% to 5%.

Emulsions of the present invention comprising a mixture of phthalmic acid ammonium salt and a phthalamic acid having ratios of acid to salt varying from about 90:10 to about 10:90. Preferred ratios of acid to salt vary from about 70:30 to about 20:80. Particularly preferred ratio of salt to acid is about 80:20.

The emulsification systems of the invention also comprise polysiloxane polyalkyl polyether copolymers, i.e., silicone glycol surfactants which are also known as copolyols. The amount of silicone glycol surfactant is preferably about 0.5 to 15% by weight. A more preferable amount of the silicone glycol surfactant is about 0.5–5% of the composition.

Suitable silicone surfactants are for example high molecular weight polymers of dimethyl polysiloxane with polyoxyethylene and/or polyoxypropylene side chains, having a molecular weight of from 10,000 to 50,000 and having the structure:

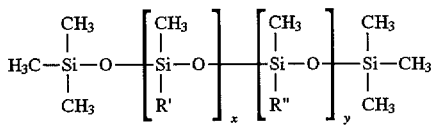

wherein the groups R' are each chosen from —H, $C_{1-18}$ alkyl and R" is —$[CH_2CH_2O]_a[CH_2(CH_2)CHO]_bH$, in which a has a value of from 9 to 115, b has a value of from 0 to 50, x has a value of from 133 to 673, y has a value of from 25 to 0.25.

Preferably, the polymer is an alkoxylated polydimethyl polymer in which:

a has a value of from 10 to 114, b has a value of from 0 to 49, x has a value of from 388 to 402, y has a value of from 15 to 0.75, the group R" having a molecular weight of from 1000 to 5000.

A more preferred alkoxylated dimethyl polysiloxane polymer is one in which:

a has the value 14, b has the value 13, x has the value 249, y has the value 1.25.

A particularly preferred copolyol is cetyl dimethicone copolyol, available from T. H. Goldschmidt as Abil® EM-90.

In addition to the high viscosity silicone material, carrier or diluent material (if any) and emulsification system, the oil phase may also comprise further ingredients such as, for example, perfume oils, coloring agents, and preservatives, etc.

The Aqueous Phase

Water-in-oil compositions of the invention comprise from 35–95% by weight, more preferably from 40–80% by weight, most preferably from 40–75% by weight of an aqueous phase.

Preferably the aqueous phase comprises 20–100% by weight of water, more preferred 30–80%, most preferred 50–70% by weight, based on the weight of the aqueous phase.

In addition to water, the aqueous phase may for example comprise one or more liquid water-miscible materials. Suitable materials are for example lower alcohols such as ethanol, and polyols such as propylene glycol, glycerol, sorbitol and polyglycerol. Suitable is the use of polyether materials such as for example polyether materials such as for example polyethyleneglycol or polypropylene glycol having a molecular weight of 100 to 500, ethoxylated polyols, e.g. Atlas G2330 ex ICI and Glucum E10 ex Amerchol and block copolymers of ethylene oxide and propylene oxide e.g. Synperonic L13 or ICI. Other humectants and/or optical brighteners may also be used.

Preferably the aqueous phase comprises 0–75% by weight of liquid water-miscible materials, more preferably 20–65%, most preferably 30–45%, based on the weight of the aqueous phase.

Another preferred ingredient for incorporation in the aqueous phase is an electrolyte material, for example selected from water soluble salts such as alkali (earth) metal salts such as sulphates, halogenides, formates, borates, benzoates, and $(C_{1-4})$tetra-alkyl ammonium halides etc. Water soluble acids such as citric acid, phosphoric acid etc. may also be used. The preferred level of electrolyte materials is from 0–25%, more preferred 1–10%, most preferred 2–5%, based on the aqueous phase. Electrolyte materials have the advantage of providing increased stability to compositions of the invention and can be used for modification of composition viscosity.

Physical Form

Water-in-oil emulsions according to the invention may take a variety of physical forms, for example they may be liquids, gels, pastes, etc. Preferably emulsions of the invention are gels having a viscosity of 5000 to $10^9$, more preferably 10,000 to 200,000 at 25° C., as measured in a Brookfield RVT viscometer, spindle #5, 50 rpm.

Other Ingredients

Water-in-oil emulsions of the invention may also include minor amounts of other ingredients such as surfactants, antibacterial agents, antidandruff agents, pearlescers, dyes, preservatives, sunscreens, viscosity modifiers, proteins, polymers, buffering agents, herb extracts, oils etc.

Other components that may be included in the emulsions include ultraviolet protection agents such as benzophenones, octyl salicylate, octyl methoxy cinnamate, and para-aminobenzoic acid, amido carboxylates (functionalized metallo soaps) such as lauryl succinamate aluminum stearate (lactate) (see e.g., U.S. Pat. Nos. 4,675,422 and 4,724,174), vitamins, and cationic surfactants. Other additives can be optionally suspended in the emulsions, e.g., graphite, abrasives such as kaopolite and snow floss silica, and waxes such as carnuba wax, paraffin wax and microcrystalline waxes.

Method of Preparation

Water-in-oil emulsions of the invention may be prepared by any suitable method for the preparation of water-in-oil emulsions. A preferred method involves the separate preparation of the oil phase and the aqueous phase by mixing, followed by gradually adding the aqueous phase to the oil phase under stirring.

Subsequent to adding the aqueous phase to the oil phase, the pH of the mixture must be raised to a value of about 5–10. In more preferred water-in-oil emulsions, the pH is about 7–9. The pH of the mixture prior to raising it to a value within the critical range is typically about 2–3. At this acidic pH, the emulsions of the invention having higher amounts of oil are unstable.

The desired pH value can be attained by addition of any suitable basic compound. Examples of such compounds include organic amines and various hydroxide salts. Representative amines are, for example, monoethanolamine, diethylamine and triethanolamine, as well as triethylamine. Suitable hydroxide salts include sodium, potassium and ammonium hydroxide. A particularly preferred base is triethanolamine (TEA).

The invention is illustrated further by the following examples which are not to be construed as limiting the invention in scope or spirit to the specific procedures described in them.

EXAMPLE 1

Water-in-oil emulsions were prepared by first preparing an oil phase comprising the phthalic anhydride derivative, Stepan TAB®-2, a 30:65 mixture of N,N-di(hydrogenated) tallow ammonium N,N-di(hydrogenated) tallow phthalamate and N, N-di(hydrogenated) tallow phthalamic acid, (unless specifically excluded in comparative examples), silicone glycol surfactant, and oil and heating to about 160°–165° F., subsequently preparing an aqueous phase at 160°–165° F. and adding it to the oil phase. After the aqueous phase has been added to the oil phase, the mixture is mixed for about 2–5 minutes at which time the base is added in an amount sufficient to attain the requisite pH. This mixture was emulsified for 25 to 30 minutes while maintaining the temperature between 150°–155° F. At this time, additional oil may be added to the emulsion and homogenization performed as needed.

The component amounts in the formulations of the following examples are given in weight percent.

EXAMPLE 2

| INGREDIENTS | Wt. % (AS IS) |
|---|---|
| Silicone DC 344 (Cyclomethicone) | 20.0 |
| Stepan TAB-2[1] | 3.0 |
| Abil EM-90[2] | 2.0 |
| Silicone DC 200 (350 CPS) (Dimethicone) | 5.0 |
| Triethanolamine 99% | Q.S. to pH 8.5 |
| DI Water | Q.S. to 100.0 |

[1] A blend of N,N-di(hydrogenated) tallow phthalmic acid and N,N-di(hydrogenated) tallow ammonium N,N-di(hydrogenated) tallow phthalamate and triethanolammoniumN,N-di(hydrogenated) tallow phthalamate and an acid to salt weight ratio of 60 to 40.
[2] Cetyl dimethicone copolyol.

EXAMPLE 3

Table 1 shows the stability of formulations prepared essentially according to Example 1 at varying levels of phthalamate and silicone surfactant.

TABLE 1

| | | STABILITY | | | | |
|---|---|---|---|---|---|---|
| | | 24 hours | | one week | | |
| % TAB-2 | % Abil EM-90 | room temp. | 42° C. | room temp. | 42° C. | 3 freeze thaw cycles |
| — | 2.0 | sep.[1] | sep. | — | — | Fail |
| 3.0 | — | sep. | sep. | — | — | Fail |
| 0.5 | 2.0 | sep. | sep. | — | — | Pass |
| 1.0 | 2.0 | stable | sep. | stable | — | Pass |
| 2.0 | 2.0 | stable | stable | stable | sep. | Pass |
| 3.0 | 1.0 | stable | stable | stable | sep. | Pass |
| 3.0 | 2.0 | stable | stable | stable | stable | Pass |
| 4.0 | 2.0 | stable | stable | stable | stable | Pass |
| 4.0 | 3.0 | stable | stable | stable | stable | Pass |
| 5.0 | 2.0 | stable | stable | stable | stable | Pass |
| 20.0 | 2.0 | stable | stable | stable | stable | Pass |
| 3.0 | 20.0 | stable | sep. | stable | sep. | Pass |

[1] emulsion separated into oil and water layers

EXAMPLE 4

Table 2 shows the stability of compositions prepared with different ratios of cyclomethicone and dimethicone and the total level of the two silicones.

TABLE 2

| | | STABILITY | | | | |
|---|---|---|---|---|---|---|
| | | 24 hours | | one week | | |
| % volatile silicone[1] | % dimethicone[2] | RT | 42° C. | RT | 42° C. | 3 Freeze-thaw cycles |
| 4.0 | 1.0 | sep. | sep. | — | — | Fail |
| 8.0 | 2.0 | sep. | sep. | — | — | Fail |
| 16.0 | 4.0 | stable | stable | stable | stable | Pass |
| 20.0 | 5.0 | stable | stable | stable | stable | Pass |
| 30.0 | 3.0 | stable | stable | stable | stable | Pass |
| 40.0 | 3.0 | stable | stable | stable | stable | Pass |
| 48.0 | 12.0 | stable | stable | sep. | sep. | Pass |
| 56.0 | 14.0 | sep. | sep. | — | — | Fail |

[1] Silicone DC 344 or DC345
[2] Silicone DC 200

EXAMPLE 5

Table 3 shows the effect of varying the base on the stability of emulsions.

TABLE 3

| | STABILITY | | | |
|---|---|---|---|---|
| | 24 hours | | one month | |
| Neutralizing Agent | room temp. | 42° C. | room temp. | 42° C. |
| Monoethanolamine | stable | stable | stable | stable |
| Triethanolamine | stable | stable | stable | stable |
| NaOH | stable | stable | stable | stable |
| Morpholine | stable | sep. | stable | — |
| NH₄OH | stable | stable | stable | sep. |

EXAMPLE 6

Table 4 shows the effect of varying the pH on the stability of emulsions having essentially the same composition as Formula 1.

TABLE 4

| | Stability | | | | |
|---|---|---|---|---|---|
| | 24 hours | | one week | | 3 Freeze-Thaw |
| pH[1] | RT | 42° C. | RT | 42° C. | Cycles |
| 2.5[2] | sep. | sep. | sep. | sep. | Fail |
| 3.5 | stable | stable | sep. | sep. | Fail |
| 4.0 | stable | stable | sep. | sep. | Fail |
| 4.5 | stable | stable | stable | stable | Fail |
| 5.5 | stable | stable | stable | stable | Pass |
| 6.5 | stable | stable | stable | stable | Pass |
| 8.0 | stable | stable | stable | stable | Pass |
| 9.0 | stable | stable | stable | stable | Pass |
| 10.0 | stable | stable | stable | stable | Pass |

[1] unless indicated otherwise, each specific pH value was attained by addition of sufficient neutralizing agent (triethanolamine)
[2] no triethanolamine present

EXAMPLE 7

Auto polish formulations were prepared essentially as described above to have the following compositions.

TABLE 5

| Ingredient | A Wt. % | B Wt. % | C Wt. % | D Wt. % |
|---|---|---|---|---|
| Silicone DC 344 | 25.0 | 30.0 | 30.0 | 20.0 |
| Stepan TAB 2 | 1.5 | 1.5 | 1.0 | 3.0 |
| Abil EM-90 | 1.0 | 1.0 | 0.75 | 2.0 |
| Silicone DC 200 (50 cps) | 3.0 | — | — | — |
| Silicone DC 200 (100 cps) | — | 2.0 | — | — |
| Silicone DC 200 (5000 cps) | — | — | 1.0 | — |
| Silicone GE 1706[1] | — | — | — | 5.0 |
| Triethanolamine, 99% | all Q.S. to pH 8.5 | | | |
| DI Water | all Q.S. to 100% | | | |
| 24 hour stability | | | | |
| room temperature | stable | stable | stable | stable |
| 42° C. | stable | stable | stable | stable |
| one week stability | | | | |
| room temperature | stable | stable | stable | stable |
| 42° C. | stable | stable | stable | stable |
| Stability after three freeze-thaw cycles | Pass | Pass | Pass | Pass |

[1]aminofunctional silicone

EXAMPLE 8

Auto polish emulsions were prepared essentially as described above to have the following compositions.

TABLE 6

| Ingredient | A Wt. % | B Wt. % | C Wt. % |
|---|---|---|---|
| Isopar M | — | — | 10.0 |
| Mineral Spirits | 5.0 | 25.0 | — |
| Stepan TAB-2 | 1.0 | 1.0 | 3.0 |
| Abil EM-90 | 0.75 | 0.75 | 2.0 |
| Silicone DC200 (350 cps) | 3.0 | 3.0 | 5.0 |
| Silicone DC 344 | 25.0 | — | 10.0 |
| Triethanolamine, 99% | all Q.S. to pH 8.5 | | |
| DI Water | all Q.S. to 100% | | |

EXAMPLE 9

Water-in-oil personal care emulsions were prepared essentially as described above to have the following compositions.

TABLE 7

| Ingredient | A Wt. % | B Wt. % | C Wt. % | D Wt. % | E Wt % |
|---|---|---|---|---|---|
| Silicone DC 344 | | 20.0 | 20.0 | 20.0 | |
| Silicone DC 200 (350 cps) | | 5.0 | | | 2.5 |
| Stepan TAB-2 | 2.0 | 3.0 | 1.5 | 1.5 | 1.5 |
| Abil EM-90 | 1.0 | 1.0 | 1.0 | 1.0 | 1.0 |
| Octyl Palmitate | 20.0 | | | | |
| Isopropyl Palmitate | | 10.0 | | | |
| White Petrolatum | | | | 5.0 | 15.0 |
| Lanolin | | | 5.0 | | |
| Methyl Paraben[1] | 0.15 | 0.15 | 0.15 | 0.15 | 0.15 |
| Propyl Paraben[2] | 0.01 | 0.01 | 0.01 | 0.01 | 0.01 |
| Glydant[3] | 0.25 | 0.25 | 0.25 | 0.25 | 0.25 |
| Triethanolamine, 99% | all Q.S. to pH 7.0 | | | | |
| DI Water | all Q.S. to 100.0 | | | | |

[1]water soluble preservative
[2]oil soluble preservative
[3]preservative

EXAMPLE 10

Lubricant-containing emulsions were prepared essentially as described above to have the following compositions.

TABLE 8

| Ingredient | A Wt. % | B Wt. % | C Wt. % |
|---|---|---|---|
| TAB-2 | 3.0 | 3.0 | 2.0 |
| Abil EM-90 | 2.0 | 2.0 | 1.5 |
| PB/Graphite[1] | 15.0 | 15.0 | |
| Ethylflow PAO-170[2] | | | 60.0 |
| Indapol L-14[3] | 10.0 | | |
| Stepan C68[4] | | 10.0 | 10.0 |
| Triethanolamine, 99% | Q.S. to pH 9.0 | | |
| DI Water | Q.S. to 100.0 | | |

[1]polybutene/graphite (lubricant)
[2]polyalpha olefin (lubricant)
[3]polybutene
[4]methyl esters of fatty acids having 18 carbon atoms (10% saturated, 11% diunsaturated, 70% monounsaturated, and 9% other)

Comparative Example 1

An antiperspirant formulation, S1 in Table 9 below, was prepared according to the description set forth in Example 6 of U.S. Pat. No. 5,188,823. As indicated in the table, this formulation had a pH of about 4 and was stable for at least one week at both ambient temperature and at 43° C.

A similar formulation, S2 in Table 9 below, was prepared with the active antiperspirant agent, Dow Corning AZG 370, being replaced by the same amount of water. This formulation had a pH of about 2.5 and separated into oil and water layers at room temperature within a few hours after preparation.

TABLE 9

| | S1 | S2 |
|---|---|---|
| Silicone DC 344 | 30.0 | 30.0 |
| TAB-2 | 2.5 | 2.5 |
| Abil B-9806 | 3.0 | 3.0 |
| DC AZG-368 (31% sol.) | 64.5 | — |
| Deionized water | Q.S. | Q.S. |
| pH | 4.0 | 2.5 |
| stability (room temperature) | at least one week | separated within few hours of preparation |
| stability (43° C.) | at least one week | not done |
| weight ratio of oil phase to aqueous phase | 1:1.5 | 1:2.15 |

Comparative Example 2

Six (6) formulations were prepared according to the procedures described in Canadian Patent Application 2,056,859 to have pH values of 5 and 7 as shown below in Table 10. Table 10 also shows the relative amounts, based on 100 parts of formulation, of the aqueous and oil phases of each formulation. The composition of the aqueous and oil phases of these formulations is given below in Tables C1 and C2.

TABLE C1

| Aqueous Phase | |
|---|---|
| Water/citric acid[1] | 51.8 |
| Glycerol | 40.7 |
| Carbowax Sentry PEG 400 | 5.0 |
| Sodium Chloride | 1.9 |
| Sodium Benzoate | 0.6 |

[1]Citric acid was added in an amount sufficient to give pH values in the final compositions of 5 or 7.

TABLE C2

| Oil Phase | |
|---|---|
| Silicone TP 504 | 64.7 |
| Diluent DC 3225 | 34.8 |
| Perfume | 0.5 |

TABLE 10

| | Formulation | | | | | |
|---|---|---|---|---|---|---|
| | R1 | R2 | R3 | R4 | R5 | R6 |
| Water phase | 79.9 | 79.9 | 70.0 | 70.0 | 60.0 | 60.0 |
| Oil phase | 20.1 | 20.1 | 30.0 | 30.0 | 40.0 | 40.0 |
| pH | 5 | 7 | 5 | 7 | 5 | 7 |
| Observation on stability | Sep.[2] | Sep. | Sep. | Sep. | Sep. | Sep. |

[2]Composition separated into layers immediately after agitation.

Formulations R1 and R2, having aqueous phase to oil phase ratios of approximately 80:20, are not stable emulsions. Each of these formulations separated immediately after agitation into two phases at ambient temperture. Similarly, formulations R3–R6, having aqueous phase to oil phase ratios as described above in Table 10, also immediately separated into oil and water layers at ambient temperature immediately after agitation. Thus, these formulations are not stable emulsions.

From the foregoing it will be appreciated that, although specific embodiments of the invention have been described herein for purposes of illustration, various modifications may be made without deviating from the spirit and scope of the invention.

What is claimed is:

1. A water-in-oil emulsion comprising:

(a) water;

(b) from about 10 to 65% by weight of an oil; and (c) an emulsification system comprising a polysiloxane polyalkyl polyether copolymer and a phthalic anhydride derivative, the phthalic anhydride derivative having the formula:

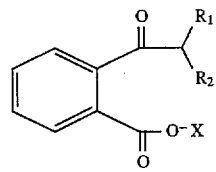

where
X is a cation is selected from the group consisting of hydrogen ion, $+NH_2R_3R_4$ where $R_3$ and $R_4$ are the same or different and represent hydrogen or straight or branched chain alkyl groups having 8–40 carbon atoms, and $R_1$ and R2 are the same or different and represent straight or branched chain alkyl groups having an average of about 8–40 carbon atoms, the emulsification system substantially permanently maintaining the water and oil as an emulsion, and the emulsification system being substantially free from aluminum and zirconium salts, the emulsion being at a pH of from about 5–10.

2. An emulsion according to claim 1, wherein the oil is a dimethicone, cyclomethicone, amino functional silicone or a mixture thereof.

3. An emulsion according to claim 2, wherein the phthalic anhydride derivative is selected from the group consisting of N,N-di(hydrogenated) tallow phthalamic acid, N,N-di (hydrogenated) tallow ammonium N,N-di(hydrogenated) tallow phthalamate, triethanolammonium N,N-di (hydrogenated) tallow phthalamate, N,N-distearyl phthalamic acid, N,N-distearyl phthalamic acid N,N-distearyl ammonium salt, and mixtures thereof.

4. An emulsion according to claim 3, wherein the phthalic anhydride derivative is selected from the group consisting of mixtures of N,N-di(hydrogenated) tallow ammonium N,N-di(hydrogenated) tallow phthalamate and N,N-di (hydrogenated) tallow phthalamic acid at salt:acid weight ratios of about 80:20, and mixtures of N,N-distearyl phthalamic acid and N,N-distearyl ammonium N,N-distearyl phthalamate.

5. An emulsion according to claim 2, wherein the oil comprises a mixture of cyclomethicone and dimethicone at a ratio of cyclomethicone to dimethicone of from about 1:3 to 60:1.

6. An emulsion according to claim 5, wherein the polysiloxane polyalkyl polyether copolymer is a blend of cetyl dimethicone copolyol and cetyl dimethicone.

7. An emulsion according to claim 6, wherein the phthalic anhydride derivative is a mixture of N,N-di(hydrogenated) tallow ammonium N,N-di(hydrogenated) tallow phthalamate and N,N-di(hydrogenated) tallow phthalamic acid at a salt acid weight ratio of about 80:20.

8. An emulsion according to claim 7, wherein the pH is from about 7–9.

9. A method for preparing a water-in-oil emulsion comprising the steps:

(a) preparing an oil phase by mixing an oil with an emulsification system comprising a phthalic anhydride derivative, a polysiloxane polyalkyl polyether copolymer and the emulsification system being substantially free from aluminum and zirconium salts, the phthalic anhydride derivative having the formula:

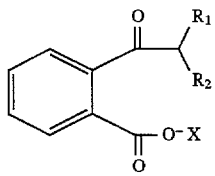

where
X a cation is selected from the group consisting of hydrogen ion, $+NH_2R_3R_4$ where $R_3$ and $R_4$ are the same or different and represent hydrogen or straight or branched chain alkyl groups having 8–40 carbon atoms, and $R_1$ and $R_2$ are the same or different and represent straight or branched chain alkyl groups having an average of 1–40 carbon atoms;

(b) preparing an aqueous phase;
(c) adding the aqueous phase to the oil phase with agitation;
(d) raising the pH to from about 5 to 10; and
(e) emulsifying the mixture.

10. A method according to claim 9, further comprising a homogenization step.

11. A method according to claim 9, wherein the oil is a dimethicone, cyclomethicone, amino functional silicone or a mixture thereof.

12. A method according to claim 11, wherein the phthalic anhydride derivative is selected from the group consisting of mixtures of N,N-di(hydrogenated) tallow ammonium N,N-di(hydrogenated) tallow ammonium N,N-di(hydrogenated) tallow phthalamate and N,N-di(hydrogenated) tallow phthalamic acid at salt:acid weight ratios of about 80:20, and mixtures of N,N-distearyl phthalamic acid and N,N-distearyl ammonium N,N-distearyl phthalamate.

13. A method according to claim 12, wherein the oil comprises a mixture of cyclomethicone and dimethicone at a ratio of cyclomethicone to dimethicone of from about 1:3 to 60:1.

14. A method according to claim 13, wherein the pH is raised to from about 7–9.

* * * * *